(12) United States Patent
Pugh et al.

(10) Patent No.: US 9,248,309 B2
(45) Date of Patent: Feb. 2, 2016

(54) LIGHT THERAPY SYSTEM INCLUDING SPECTACLE FRAMES AND CONTACT LENSES

(75) Inventors: Randall B. Pugh, Jacksonville, FL (US); William Chester Neeley, Melbourne, FL (US); Robertson Towart, Cove (GB); Mario Jozef Joanna Peeters, Meerhout (BE); Wilhelmus Drinkenburg, Molenschot (NL); Aleksandar Miletic, Moscow (RU)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 331 days.

(21) Appl. No.: 13/362,264

(22) Filed: Jan. 31, 2012

(65) Prior Publication Data

US 2012/0215291 A1     Aug. 23, 2012

(51) Int. Cl.
| | |
|---|---|
| *A61N 5/06* | (2006.01) |
| *A61M 21/02* | (2006.01) |
| *G02C 7/04* | (2006.01) |
| *G02C 11/04* | (2006.01) |
| *A61M 21/00* | (2006.01) |

(52) U.S. Cl.
CPC .............. *A61N 5/0618* (2013.01); *A61M 21/02* (2013.01); *G02C 7/04* (2013.01); *G02C 11/04* (2013.01); *A61M 2021/0044* (2013.01); *A61N 2005/063* (2013.01); *A61N 2005/0648* (2013.01)

(58) Field of Classification Search
CPC ............................. A61N 5/06; A61N 2005/06
See application file for complete search history.

(56) References Cited

U.S. PATENT DOCUMENTS

| | | | | |
|---|---|---|---|---|
| 3,578,850 | A | * | 5/1971 | Grant ........................ 351/159.02 |
| 5,137,018 | A | | 8/1992 | ChupriKov et al. |
| 5,757,458 | A | * | 5/1998 | Miller et al. ............. 351/159.02 |
| 6,235,046 | B1 | * | 5/2001 | Gerdt ............................... 607/88 |
| 6,350,275 | B1 | * | 2/2002 | Vreman et al. ................. 607/88 |
| 2004/0225340 | A1 | * | 11/2004 | Evans ............................. 607/88 |
| 2005/0237479 | A1 | * | 10/2005 | Rose ............................. 351/123 |
| 2005/0240247 | A1 | * | 10/2005 | McIlroy et al. ................. 607/88 |
| 2011/0019148 | A1 | | 1/2011 | Portney |

FOREIGN PATENT DOCUMENTS

| | | |
|---|---|---|
| WO | WO 9747993 A1 | 12/1997 |
| WO | WO 2006099413 A2 | 9/2006 |

OTHER PUBLICATIONS

International Search Report for PCT PCT/US2012/023672 Date of Mailing Jun. 1, 2012.

* cited by examiner

*Primary Examiner* — Lynsey Crandall

(57) ABSTRACT

The present invention provides for eyeglasses used together with contact lenses to deliver light therapy to the wearer. The eyeglass lenses or frames feature an embedded light source in logical and electrical communication with power, sensors, processors, and other components contained within the eyeglasses. The eyeglass lenses or frames project light into complimentary contact lenses which refract, diffract or reflect light into the wearer's eyes.

8 Claims, 11 Drawing Sheets

LIGHT THERAPY SYSTEM INCLUDING SPECTACLE FRAMES AND CONTACT LENSES

RELATED APPLICATIONS

This application claims priority to U.S. Provisional Patent Application Ser. No. 61/439,401 filed Feb. 4, 2011; the contents of which are relied upon and incorporated by reference.

FIELD OF USE

This invention describes a light therapy delivery mechanism for treatment of seasonal affective disorder (SAD) and other purposes. More specifically, in some embodiments, the invention provides eyeglasses or contact lenses or both including features for intelligent delivery of light therapy.

BACKGROUND

Seasonal affective disorder (SAD) is a well-established mood disorder wherein sufferers experience depressive symptoms in a certain season of the year, most frequently during winter months. Those affected by SAD often have normal mental health during most of the year. Symptoms of SAD may include, but are not limited to, excessive sleeping, lack of energy, craving carbohydrates, difficulty concentrating, and withdrawal from social activities. The symptoms result in feelings of depression, hopelessness, pessimism, and lack of pleasure.

Seasonal mood variations are believed to be related to changes in exposure to light. Geographic areas, such as the Arctic region, that experience fewer daylight hours, lower sunlight intensity, or significant periods of overcast skies exhibit a greater incidence of SAD. Variations in prevalence of SAD within the adult population are evident within the United States, ranging from low rates in Florida and other sunny states to notably higher rates in Alaska, New Hampshire and other northern or overcast areas.

Light therapy has been researched and established as a prominent and effective treatment for classic, or winter-based, seasonal affective disorder. Light therapy employs a device which emits significantly more lumens than a standard incandescent lamp. Common implementations include the preferred bright white full spectrum light at 10,000 lux, or optionally blue light at a wavelength of 480 nm at 2,500 lux, or green light at a wavelength of 500 nm at 350 lux. Light therapy normally requires a patient to sit with their eyes open at a prescribed distance from the light source for thirty to sixty minutes each day. This seasonal treatment is maintained for several weeks until the patient experiences frequent exposure to natural light. A majority of patients find the therapy inconvenient and a considerable percentage, in some studies up to 19%, therefore stop treatment. New methods and approaches are therefore desirable to deliver light therapy in a more convenient, continuous, and intelligent manner.

SUMMARY

Accordingly, the present invention includes eyeglasses capable of delivering light therapy to the wearer. The eyeglass lenses or frames feature an embedded light source in logical and electrical communication with power, sensors, processors, and other components contained within the temple of the eyeglasses.

In addition, in some embodiments, eyeglass lenses or frames project light into complimentary contact lenses which refract or diffract the light into the wearer's eyes.

In still another aspect, in some embodiments, spectacle frames provide sensors and power which are in wireless communication with contact lenses containing a light source for the light therapy.

Finally, contact lenses may include embedded light sources as well as supporting electronics. Eyeglasses are not included in this embodiment.

DETAILED DESCRIPTION OF THE INVENTION

Figure 1:
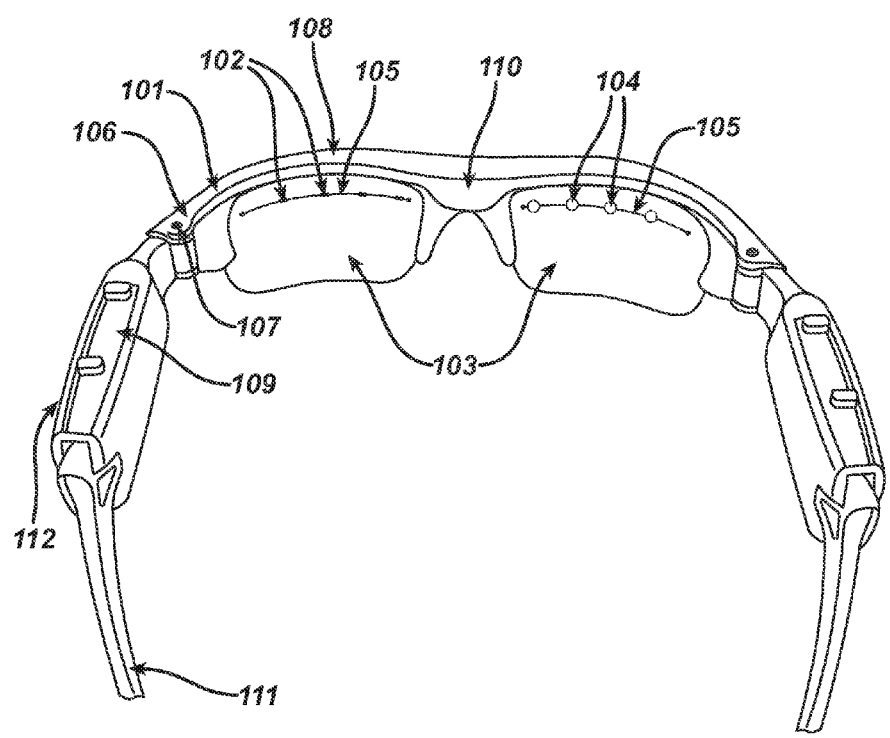
FIG. 1 illustrates a back view of eyeglasses with light sources embedded in the lenses and with supporting electronics contained within the temple according to some embodiments of the present invention.

The present invention includes methods and apparatus for delivering light therapy using eyeglasses with embedded light sources. In addition, the present invention includes delivering light therapy using a combination of eyeglasses and complimentary contact lenses. The present invention also encompasses delivering light therapy using only contact lenses with embedded light sources.

In the following sections detailed descriptions of embodiments of the invention will be given. The description of both preferred and alternative embodiments are exemplary embodiments only, and it is understood that to those skilled in the art that variations, modifications and alterations may be apparent. It is therefore to be understood that said exemplary embodiments do not limit the scope of the underlying invention.

GLOSSARY

In this description and claims directed to the presented invention, various terms may be used for which the following definitions will apply:

Complimentary contact lens: as used herein refers to contact lenses and eyeglasses with special features used together to deliver light therapy.

Contact lens: refers to any ophthalmic device that resides in or on the eye. These devices can provide optical correction or may be cosmetic. For example, the term lens can refer to a contact lens, intraocular lens, overlay lens, ocular insert, optical insert or other similar device through which vision is corrected or modified, or through which eye physiology is cosmetically enhanced (e.g. iris color) without impeding vision. In some embodiments, the preferred lenses of the invention are soft contact lenses made from silicone elastomers or hydrogels, which include but are not limited to silicone hydrogels, and fluorohydrogels.

Intelligent light therapy: as used herein refers to a method of delivering light therapy whereby a processor evaluates various data and, based on data analysis, dynamically makes compensating adjustments to a programmed light therapy schedule. Adjusting light therapy based on the user's exposure to ambient light is one example of intelligent light therapy.

Light therapy: as used herein refers to exposure to specific wavelengths of light, controlled with various devices, and administered for a specified amount of time, at a specified intensity, and, in some cases, at a specified time of day.

Lux: as used herein refers to units of illumination in the International System of Units (SI). Lux provides a measure of luminous power per area. One lux is the amount of illumination provided when one lumen is evenly distributed over an area of one square meter. This is also equivalent to the illumination that would exist on a surface all points of which are one meter from a point source of one international candle. One lux is equal to 0.0929 foot-candle.

Optical Zone: as used herein refers to an area of an ophthalmic lens through which a wearer of the ophthalmic lens sees.

Programmed light therapy schedule: as used herein refers to a set of automated instructions that controls light therapy timing, duration and intensity based on variables such as dates, geographic region, and severity of a user's seasonal affective disorder symptoms. A programmed light therapy schedule may be set by an eye care professional, a medical doctor, or a user.

Seasonal Affective Disorder (SAD): as used herein refers to a mood disorder that occurs during seasons when exposure to sunlight is limited, characterized by symptoms of depression and relieved by the arrival of spring or by light therapy. A recurrent state of depression, usually experienced by people in winter, thought to be related to lack of sunlight.

Referring now to FIG. 1, a back view of spectacle frames 101 with light sources 102 embedded in lenses 103 is illustrated. Light sources 102 may also be mounted on the surface of lenses 103. Light sources 102 may include light-emitting diodes (LEDs) or other lights which emit blue light at wavelengths of 450 to 500 nanometers, most preferably at 470 to 480 nanometers, and at 2,000 to 3,000 lux. Alternatively, LEDs or other lights may emit green light at wavelengths of 475 to 525 nanometers, most preferably at 490 to 510 nanometers, and at 300 to 400 lux. Additionally, the light source 102 may be secured in any other manner which allows In another embodiment, a single light source may be piped to one or more locations within an eyeglass lens 103 or eyeglass frame 101 to provide illumination. Light pipes may include, for example, fiber optic pathways.

An example of illuminated light sources is illustrated at 104. A light source 102 provides illumination toward a wearer's eyes such that an illumination is not obvious to an observer.

In another embodiment, light sources 102 are positioned such that light is directed into a lens 103. A lens 103 may include light scattering properties in areas where light is specifically directed or light scattering properties throughout a lens 103. Light scattering areas may include diffractive properties, refractive properties, reflective properties or any combination of diffractive, refractive and reflective properties. Light scattering areas act to diffuse light, achieving presentation of a soft glow rather than a glaring ray before a user's eye. In some preferred embodiments, light scattering areas may form a ring within a perimeter area of an eyeglass lens 103 and may include an internal barrier between a light scattering area and an optical zone in a central portion of a lens 103. An internal barrier prevents light intended for light therapy from being dispersed into an optical zone of a lens 103, minimizing the effect of light therapy luminescence on normal vision. In still other embodiments, an entire lens 103 includes light scattering properties designed such that it disperses only light of wavelengths emitted by embedded light sources 102. This embodiment supports maximum dispersion of light wavelengths intended for light therapy while not causing dispersion of light wavelengths that would affect normal vision. A lens 103 may include a coating which shields light therapy luminescence from being readily noticed by an observer while not diminishing a user's light therapy or vision.

In the present embodiment, light sources 102 are connected to one another via conductive paths 105. Conductive paths 105 may be wires embedded within a lens 103, or may be a conductive material, such as, for example, gold, copper, silver or other metal or conductive fiber applied to a surface of a lens 103 via pad printing, sputter coating, vapor deposition or other known method. Conductive paths 105 are in electrical and logical communication with supporting electronics contained within one or both temple pieces 109. In some embodiments, supporting electronics are miniaturized such that they may be contained in other areas of eyeglasses, such as, for example, in areas near a hinge 107, within a frame above a lens 108, within a bridge 110, within an earpiece 111, or other area.

One or more light sensors 106 are used to detect ambient white light, blue light or green light. Light sensors 106 may be located within an eyeglass frame 101 near a hinge 107, within a frame above a lens 108, within a temple piece 109, within a bridge 110, or other appropriate area where a sensor 106 will not be obstructed, such as by hair. A light sensor 106 is in electrical and logical communication with supporting electronics contained within one or both temple pieces 109 or other area of eyeglasses.

In some embodiments, a user control element 112, such as a switch or button, is provided to allow a user to adjust timing, duration and intensity of light therapy. One or more user control elements 112 may be present in temple pieces 109 or other areas of eyeglasses, such as, for example, in areas near a hinge 107, within a frame above a lens 108, within a bridge 110, within an earpiece 111, or other area. Some embodiments provide for a basic operational state, wherein light therapy is controlled manually by a user starting and stopping therapy at appropriate times.

According to the present embodiment, a programmed light therapy schedule may, for example, automatically adjust light therapy timing, duration and intensity based on variables such as dates, geographic region, and severity of a user's seasonal affective disorder symptoms. A programmed light therapy schedule may be set by an eye care professional, a medical doctor, or a user. During programmed light therapy, it may be desirable for a user to adjust light intensity based on an activity, such as, for example, decreasing light intensity when reading, working on a computer, or driving. Conversely, it may be desirable to increase light intensity during work breaks, lunch break, or other less visually active times. In some embodiments, intelligent light therapy is delivered when a processor evaluates manual changes to a programmed light therapy schedule and provides compensating adjustments in duration and intensity of treatment. In still other embodiments, intelligent light therapy is achieved when data from light sensors 106 is analyzed by a processor and a programmed light therapy schedule is dynamically adjusted based on a wearer's exposure to ambient light.

In another embodiment of the present invention, a user may manually adjust light therapy based on the results of blood testing for melatonin levels. Melatonin produced by the pineal gland is inhibited by light and increases with darkness. Higher levels of melatonin promote sleepiness and lethargy, symptoms of seasonal affective disorder. Analysis of the level of melatonin in a patient's blood may be used as a guide to increase or decrease light therapy.

In still other embodiments, a user may manually adjust light therapy to intentionally alter their sleep cycle. The use of light therapy for sleep cycle alteration may be valuable for persons working night shifts, for persons travelling to significantly different time zones, for military personnel preparing for night operations, and other uses. Additionally, light therapy initiated by the user upon awakening may be used to treat circadian rhythm disorders such as delayed sleep phase syndrome (DSPS) and non-24-hour sleep-wake syndrome.

Figure 2:
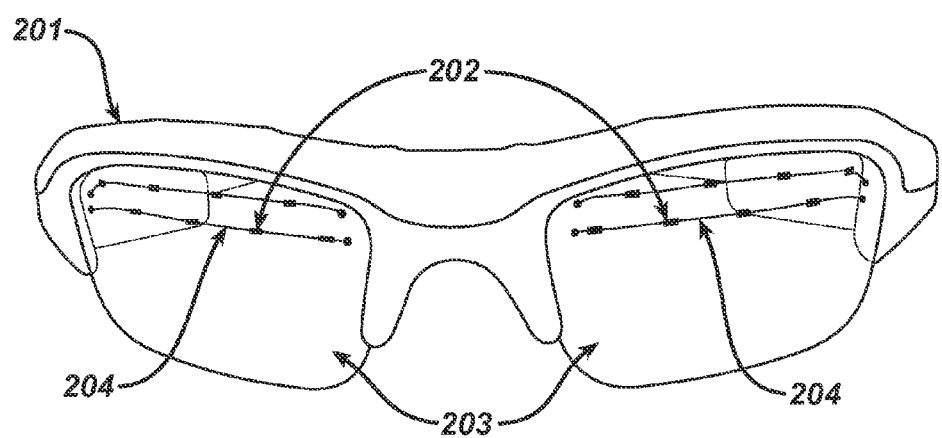
FIG. 2 illustrates a front view of eyeglasses with light sources embedded in the lenses according to some embodiments of the present invention.

Referring now to FIG. 2, a front view of spectacle frames 201 with light sources 202 embedded in lenses 203 is illustrated. Light sources 202 are connected to one another via conductive paths 204.

Figure 3:
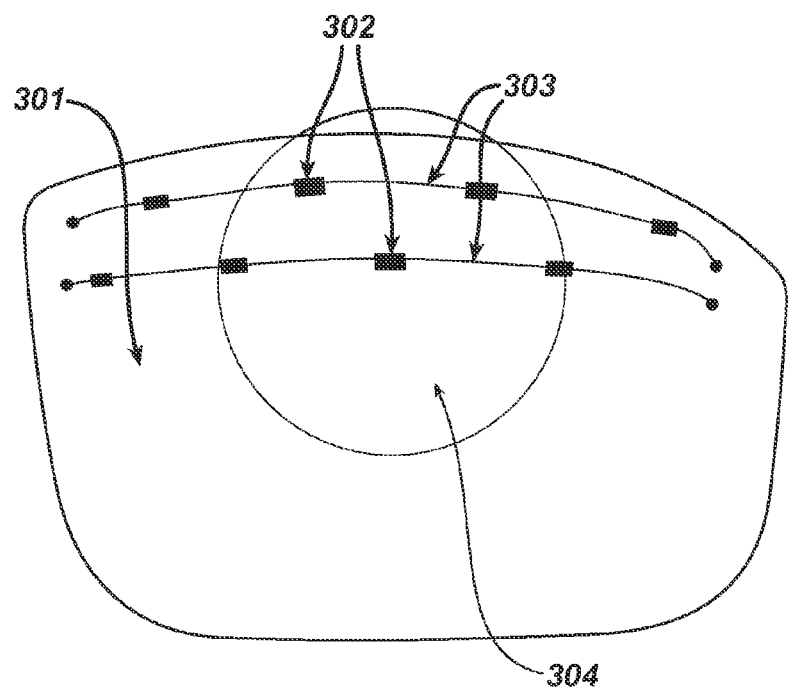
FIG. 3 illustrates a close-up view of an eyeglass lens with embedded light sources according to some embodiments of the present invention.

Referring now to FIG. 3, illustrated is a close-up view of a single eyeglass lens 301 with embedded light sources 302 connected via conductive paths 303. While the embodiment described in this application shows eight light sources 302 per lens 301, other embodiments may include fewer or more light sources 302 per lens 301 and may include light sources 302 in varying locations and patterns within a lens 301. To provide a sense of scale, a lens 301 is shown placed over a standard U.S. quarter dollar coin 304. Not shown in this diagram is a mechanism for providing electrical communication between the light sources 302 and supporting electronics. Electrical communication may be provided, for example, via a conductive contact between a source located in a temple of a pair of eyeglasses, via a conductive wire, a conductive ribbon wire, or via wireless modes, such as inductance. Inductance may be accomplished, for example, via an antenna located in the lens or the lens frame and a power source transmitting power from a temple piece or other proximate location to the antenna.

Figure 4:
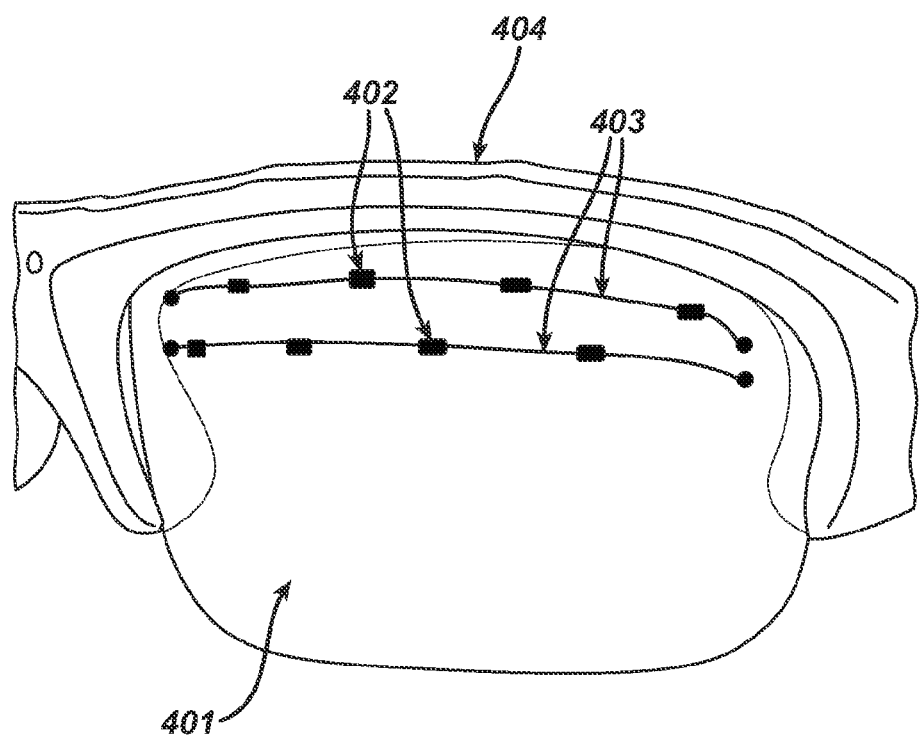
FIG. 4 illustrates a close-up view of an eyeglass lens with embedded light sources mounted in spectacle frames according to some embodiments of the present invention.

Referring now to FIG. 4, a close-up view of a single eyeglass lens 401 with embedded light sources 402 connected via conductive paths 403 is illustrated mounted into an eyeglass frame 404.

Figure 5:
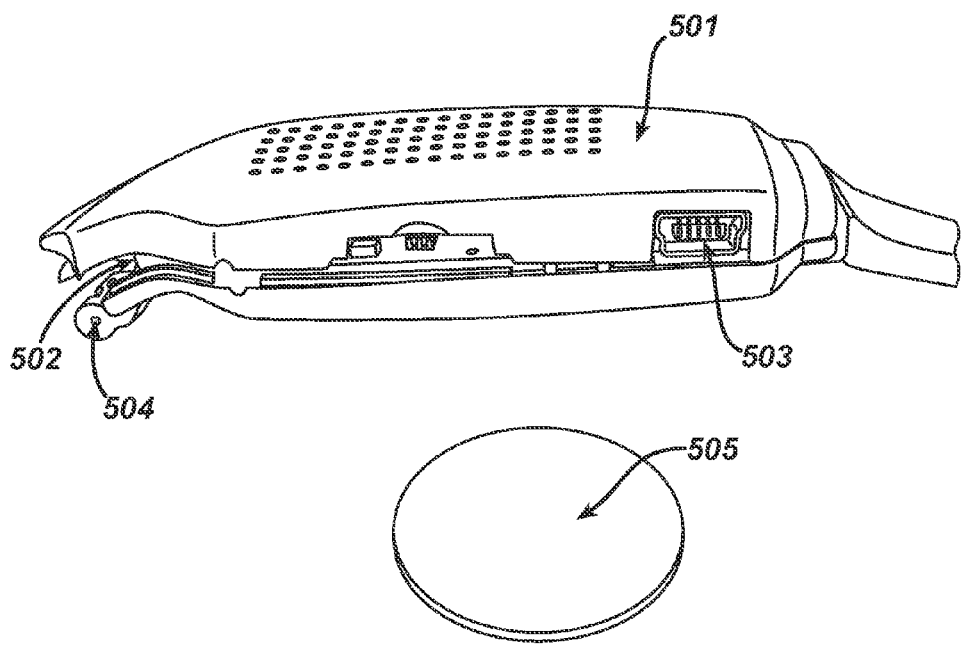
FIG. 5 illustrates a portion of an eyeglass temple piece housing supporting electronics according to some embodiments of the present invention.

Referring now to FIG. 5, illustrated is a close-up view of a portion of an eyeglass temple piece 501 which houses supporting electronics. The temple piece 501 is not fully closed as evidenced by a gap 502. A USB connector 503 is used for electrical connection, such as, for example, charging batteries within a temple piece 501. A USB connector 503 is also used for logical communication, such as, for example, loading a user-specific programmed light therapy schedule or offloading usage and sensor data stored by supporting electronics. A hinge area 504 is visible, at which point a temple piece 501 connects to an eyeglass frame. For scale purposes, a temple piece 501 is shown adjacent to a standard U.S. quarter dollar coin 505.

Figure 6:
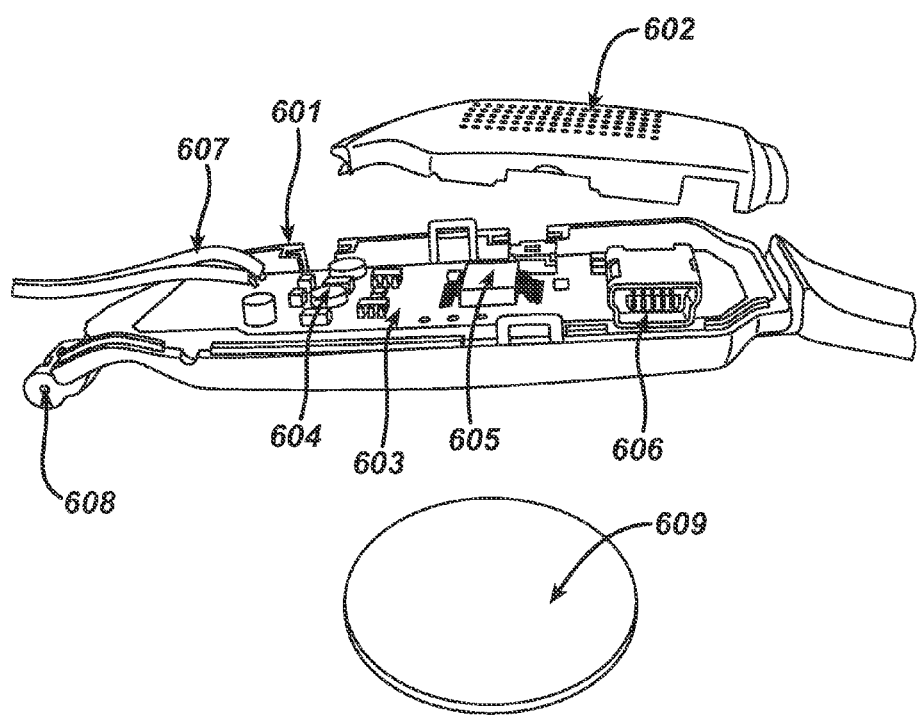
FIG. 6 illustrates a portion of an eyeglass temple piece opened to show supporting electronics according to some embodiments of the present invention.

Referring now to FIG. 6, a close-up of an eyeglass temple piece 601 is now illustrated with a top half of a supporting electronics casing 602 removed. A circuit board containing supporting electronics 603 is displayed including batteries 604, a processor 605 and a USB connector 606. Wiring 607 provides logical and electrical communication between supporting electronics 603 and other components such as light sources and light sensors. A hinge area 608 is visible, where a temple piece 601 connects to an eyeglass frame. To provide a sense of scale, a temple piece 601 is shown adjacent to a standard U.S. quarter dollar coin 609.

Figure 7:
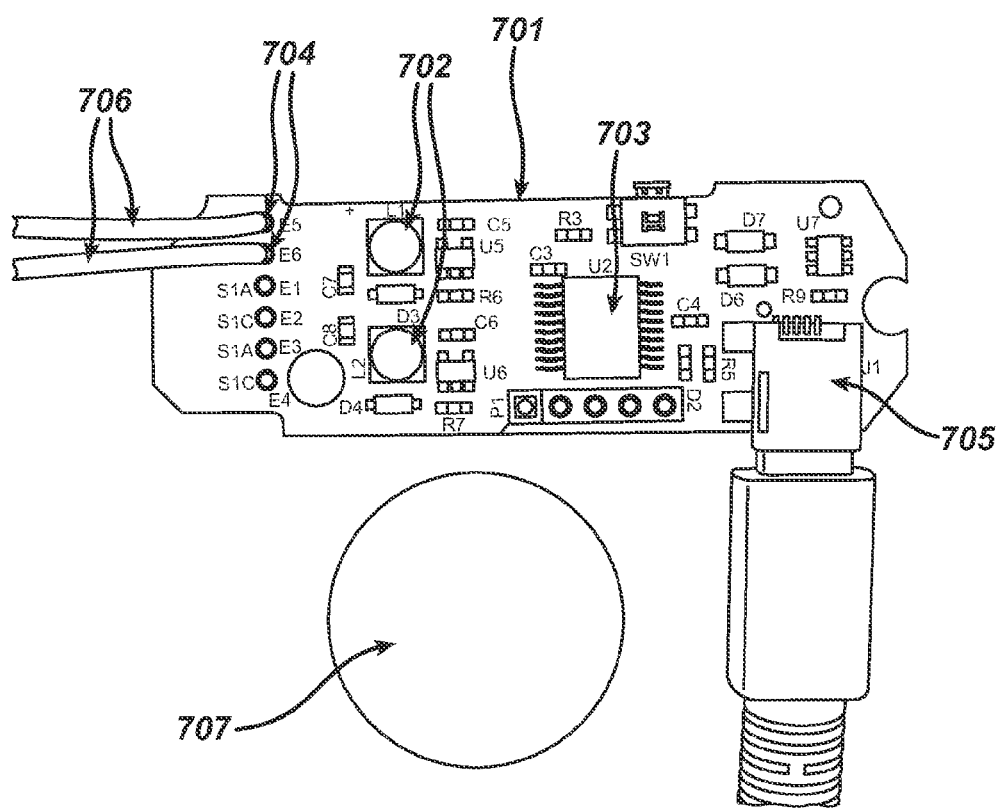
FIG. 7 illustrates one side of supporting electronics from within an eyeglass temple piece according to some embodiments of the present invention.

Referring now to FIG. 7, a top down view of a first side of a circuit board containing supporting electronics 701 is illustrated. The circuit board 701 is shown removed from a casing in which it was depicted in FIGS. 5 and 6. A circuit board 701 includes batteries 702, a processor 703, power terminals 704, and a USB connector 705. Wiring 706 attached to power terminals 704 provides logical and electrical communication between supporting electronics on a circuit board 701 and other components such as light sources and light sensors. A processor 703 may be used, for example, to run programmed light therapy schedules stored in memory, to analyze light sensor data and determine a unique light therapy schedule based on the wearer's exposure to ambient light, to evaluate manual changes to a programmed light therapy schedule and provide compensating adjustments, and to analyze light source and light sensor data to detect device failures. Power terminals 704 enable connection of wiring 706, allowing logical and electrical communication between supporting electronics on a circuit board 701 and other components such as light sources and light sensors. To provide a sense of scale, a circuit board 701 is shown adjacent to a standard U.S. quarter dollar coin 707.

Figure 8:
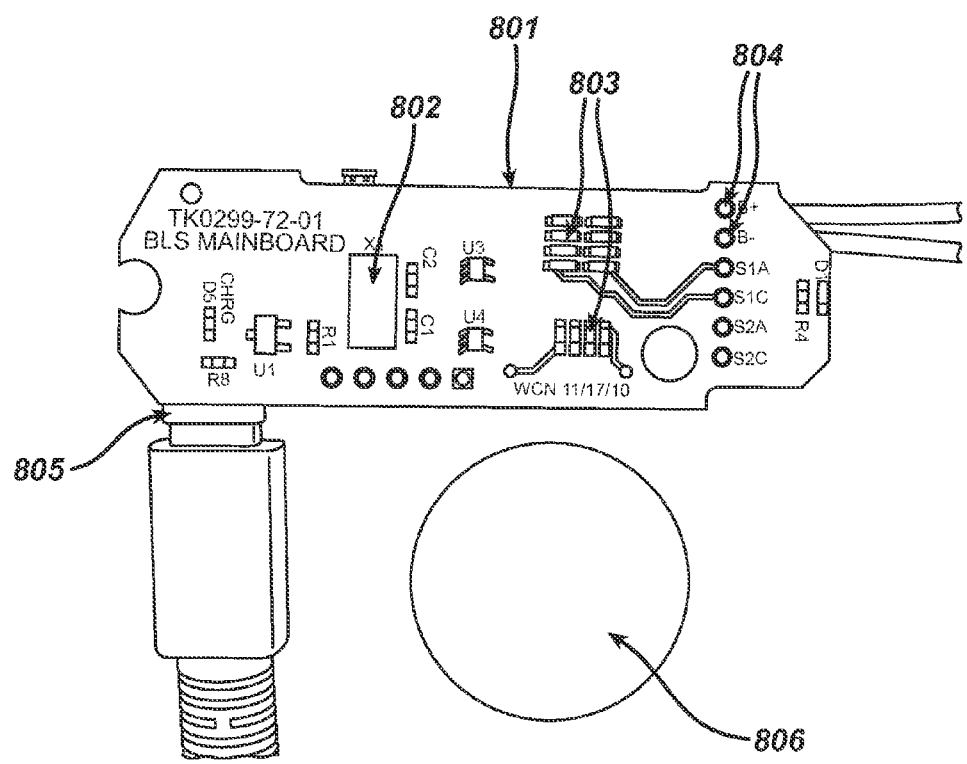
FIG. 8 illustrates a second side of supporting electronics from within an eyeglass temple piece according to some embodiments of the present invention.

Referring now to FIG. 8, illustrated is a top down view of a second side of a circuit board containing supporting electronics 801. The circuit board 801 is shown removed from a casing in which it was depicted in FIGS. 5 and 6. A circuit board 801 includes memory 802, capacitors 803, and power terminals 804. The USB connector of FIG. 7 (705) is seen in FIG. 8 at 805. For scale, a circuit board 801 is shown adjacent to a standard U.S. quarter dollar coin 806. Memory 802 may be used, by way of non-limiting example, to store pre-programmed light therapy schedules, to store data captured by light sensors, to store actual light therapy dates, times, durations and intensities, and to store data related to light source and light sensor operation in order to detect device failures.

Figure 9:
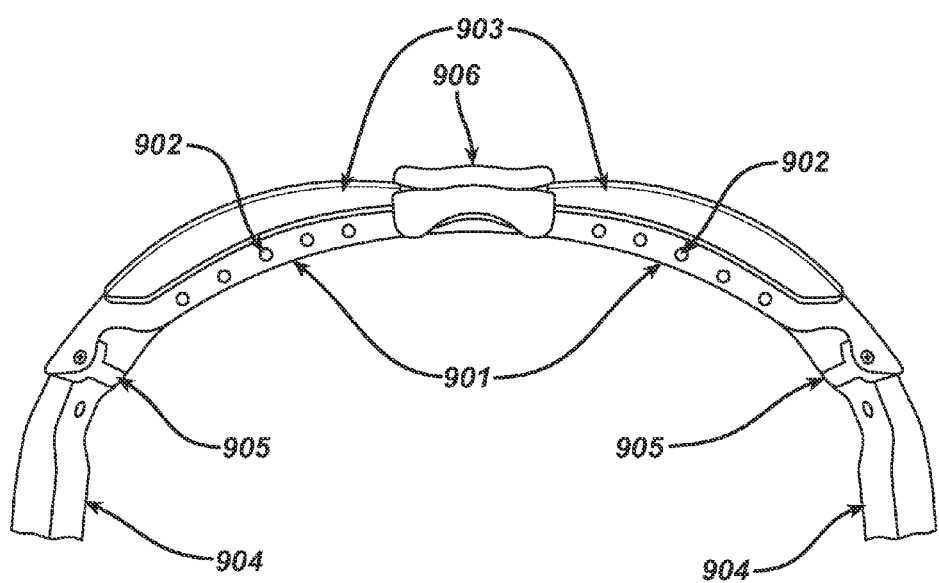
FIG. 9 illustrates a bottom view of eyeglasses with light sources embedded in the frame according to some embodiments of the present invention.

Referring now to FIG. 9, illustrated is a bottom view of an eyeglass frame 901 with light sources 902 embedded in the eyeglass frame 901 above lenses 903. Light sources 902 may be embedded within an eyeglass frame 901, or may be mounted on a surface of an eyeglass frame 901. Light sources 902 are connected to one another by conductive paths, not illustrated in FIG. 9. Conductive paths may be wires embedded within an eyeglass frame 901, or may be a conductive material, such as, for example, gold, silver, copper or other metallic material or conductive fiber applied to the surface of an eyeglass frame 901 via pad printing, sputter coating, vapor deposition or other known method. Conductive paths allow light sources 902 to be in electrical and logical communication with supporting electronics housed within one or both temple pieces 904. In some embodiments, supporting electronics are miniaturized such that they may be contained in other eyeglass areas, such as, for example, in areas near a hinge 905, within a frame above a lens 901, within a bridge 906, within an earpiece (not shown in FIG. 9), or other area. Light sources 902 are positioned so that light is directed onto lenses 903. Lenses 903 may include light scattering properties in areas where light is specifically directed or light scattering properties throughout the lens. Light scattering areas may include diffractive properties, refractive properties, reflective properties or any combination of diffractive, refractive and reflective properties. Light scattering areas act to diffuse light, achieving presentation of a soft glow rather than a glaring ray before a user's eye. Lenses 903 may include a coating which shields light therapy illumination from being readily noticed by an observer while not affecting a user's light therapy or vision.

Figure 10:
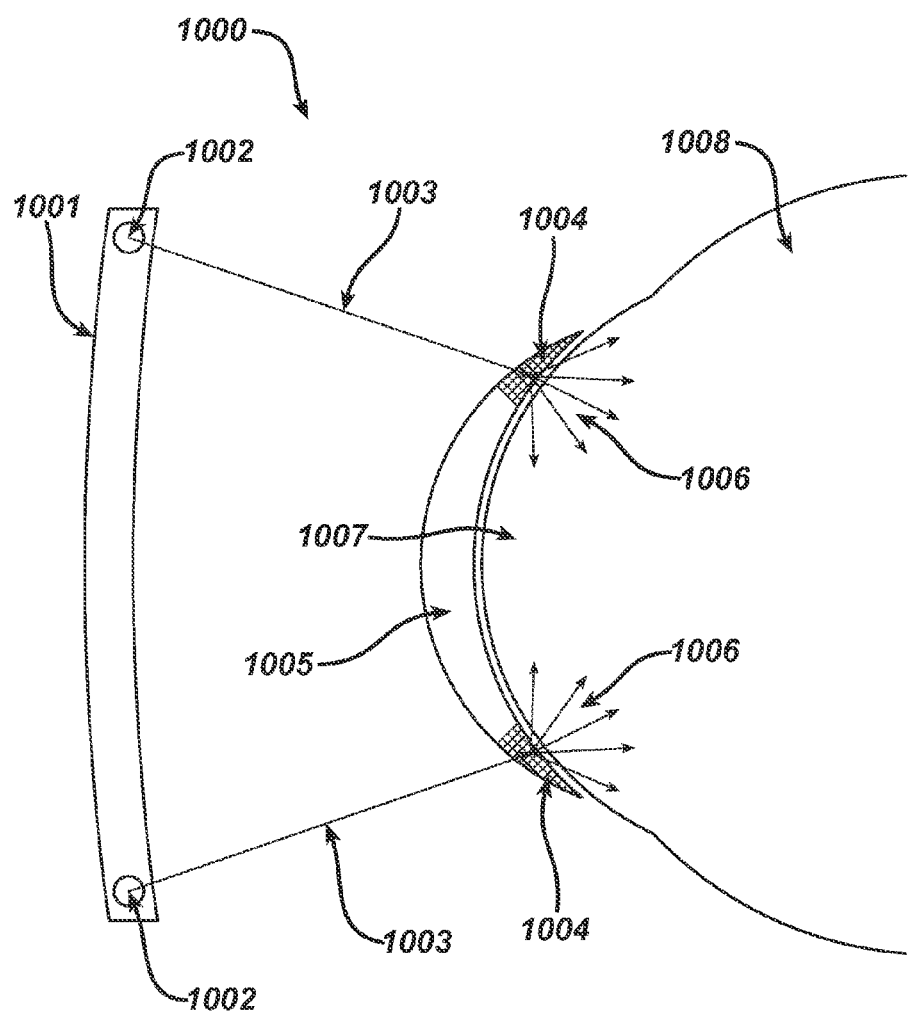
FIG. 10 illustrates a cross-section view of an eyeglass lens with embedded light sources directing light into a complimentary contact lens according to some embodiments of the present invention.

Referring now to FIG. 10, an embodiment including a complimentary contact lens is illustrated. A cross-section view 1000 includes an eyeglass lens 1001 with embedded light sources 1002 directing light 1003 into light scattering areas 1004 of a complimentary contact lens 1005. A light scattering area 1004 results in light 1006 being dispersed across a cornea 1007 of an eye 1008. A light scattering area 1004 may include diffractive properties, refractive properties, reflective properties or any combination of diffractive, refractive and reflective properties.

In some embodiments, a cross-section view 1000 may be a top-down view, wherein one or more embedded light sources 1002 are placed near the sides of an eyeglass lens 1001. In other embodiments, a cross-section view 1000 may be a side view, such that one or more embedded light sources 1002 are placed near the top and bottom of an eyeglass lens 1001. In still other embodiments, embedded light sources 1002 may be embedded in or mounted on an eyeglass frame rather than an eyeglass lens 1001. Embedded light sources 1002 include light-emitting diodes (LEDs) or other light sources 1002 emitting light 1003 for light therapy. Light sources 1002 may include light-emitting diodes (LEDs) or other lights which emit blue light at wavelengths of 450 to 500 nanometers, most preferably at 470 to 480 nanometers, and at 2,000 to 3,000 lux. Alternatively, LEDs or other lights may emit green light at wavelengths of 475 to 525 nanometers, most preferably at 490 to 510 nanometers, and at 300 to 400 lux. Another embodiment includes a single light source from which light is piped to one or more locations within an eyeglass lens 1001 or eyeglass frame to provide illumination.

Supporting electronics, not shown, are contained in an eyeglass frame and include components such as, for example, light sensors, batteries, capacitors, memory, processors, and a USB connector. Supporting electronics are in logical and electrical communication with light sources 1002. Electrical communication may be provided, for example, via a conductive contact between a source located in a temple of a pair of eyeglasses, via a conductive wire, a conductive ribbon wire, or via wireless modes, such as inductance. Inductance may be accomplished, for example, via an antenna located in the lens or the lens frame and a power source transmitting power from a temple piece or other proximate location to the antenna.

In some embodiments, light scattering areas 1004 of a complimentary contact lens 1005 form a ring within a perimeter area of a complimentary contact lens 1005 such that directed light 1003 need not strike a limited target area. The orientation of a complimentary contact lens 1005 on an eye 1008 relative to light sources 1002 within an eyeglass lens 1001 is therefore inconsequential when light 1003 is directed toward a light scattering area 1004 continuously present around a perimeter area of a complimentary contact lens 1005.

In some preferred embodiments, a complimentary contact lens 1005 may include an internal barrier between a light scattering area 1004 and an optical zone in a central portion of a lens. An internal barrier prevents light 1003 intended for light therapy from being dispersed into an optical zone of a complimentary contact lens 1005. In this way, light 1003 intended for light therapy is only dispersed around a perimeter of a cornea 1007, minimizing its effect on normal vision.

In still other embodiments, an entire complimentary contact lens 1005 includes light scattering properties such as diffraction, refraction and reflection. Light scattering properties are designed such that they disperse only light 1003 of wavelengths emitted by embedded light sources 1002. This embodiment supports maximum dispersion of light 1003 wavelengths intended for light therapy within an eye 1008 while not causing dispersion of light wavelengths that would affect normal vision.

Figure 11:
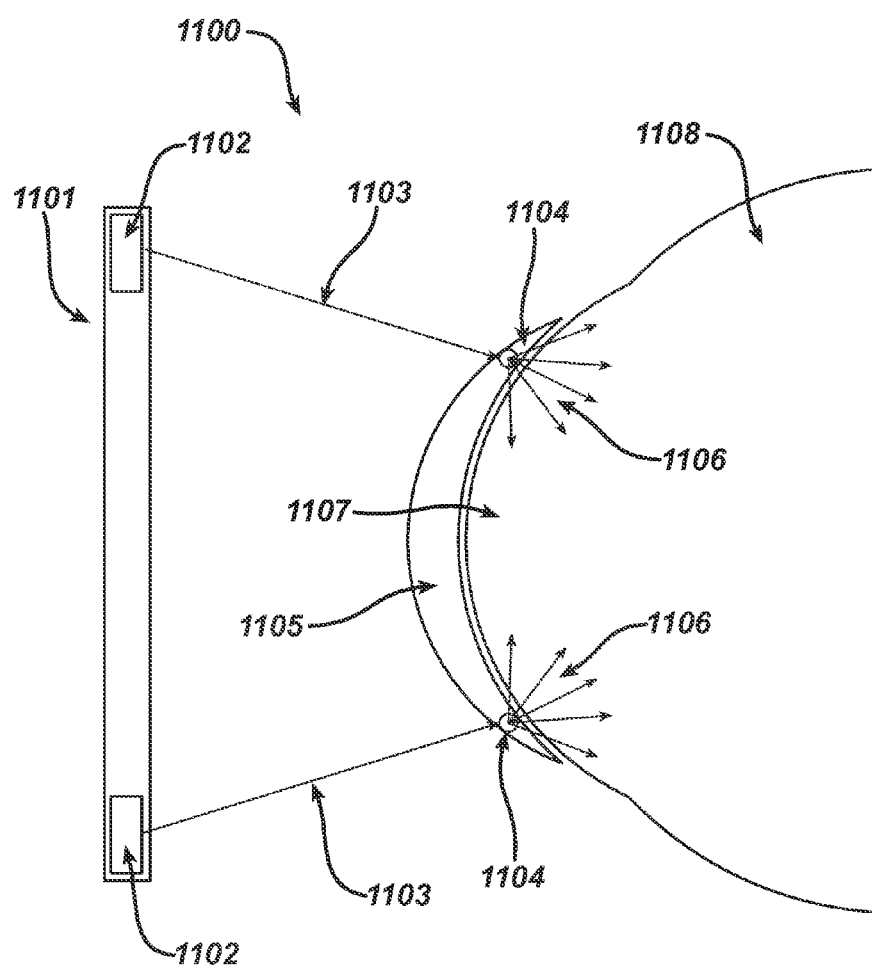
FIG. 11 illustrates a cross-section view of eyeglasses with supporting electronics in wireless communication with contact lenses containing light sources according to some embodiments of the present invention.

Referring now to FIG. 11, an embodiment is illustrated including an eyeglass frame and a complimentary contact lens. A cross-section view 1100 includes an eyeglass frame 1101 containing supporting electronics 1102. Supporting electronics 1102 may include components such as, for example, light sensors, batteries, capacitors, memory, processors, and a USB connector. Supporting electronics 1102 are in wireless communication 1103 with a complimentary contact lens 1105 containing embedded light sources 1104 directing light 1106 onto a cornea 1107 of an eye 1108. Supporting electronics 1102 may be placed in various locations embedded in or mounted on an eyeglass frame 1101. In other embodiments, supporting electronics 1102 may be included in jewelry, hats, clothing, or other items worn by a user such that light sensors detect ambient light experienced by the user and supporting electronics 1102 are near a complimentary contact lens 1105 for purposes of wireless communication. Wireless modes of communication may include, for example, inductance. Inductance may be accomplished via an antenna located in a complimentary contact lens 1105 and a power source transmitting power from an eyeglass frame 1101, jewelry, clothing, or other item proximate to the antenna.

In some embodiments of the present invention, a cross-section view 1100 may be a top-down view, wherein supporting electronics 1102 are placed near the sides of an eyeglass frame 1101. In other embodiments, a cross-section view 1100 may be a side view, such that supporting electronics 1102 are placed near the top and bottom of a side of an eyeglass frame 1101. A number of embedded light sources 1104 and an arrangement of embedded light sources 1104 around a perimeter of a complimentary contact lens 1105 may vary. Embedded light sources 1104 include light-emitting diodes (LEDs) or other light sources 1104 emitting light 1106 for light therapy. Light sources 1104 may include light-emitting diodes (LEDs) or other lights which emit blue light at wavelengths of 450 to 500 nanometers, most preferably at 470 to 480 nanometers, and at 2,000 to 3,000 lux. Alternatively, LEDs or other lights may emit green light at wavelengths of 475 to 525 nanometers, most preferably at 490 to 510 nanometers, and at 300 to 400 lux. Another embodiment includes a single light source from which light is piped to one or more locations within a complimentary contact lens 1105 to provide illumination.

In some embodiments, light sources 1104 may direct light 1106 into an interior portion of a complimentary contact lens 1105 in which the light sources 1104 are embedded. Light 1106 may be directed into a light scattering area, not depicted, including diffractive properties, refractive properties, reflective properties, or any combination of diffractive, refractive and reflective properties. A light scattering area may form a ring within a perimeter area of a complimentary contact lens 1105. Light 1106 striking a light scattering area causes a generally broad dispersion of light 1106 onto a cornea 1107 of an eye 1108.

In some preferred embodiments, a complimentary contact lens 1105 may include an internal barrier between a light scattering area around a perimeter of a lens and an optical zone in a central portion of a lens. An internal barrier prevents light 1106 intended for light therapy from being dispersed into an optical zone of a complimentary contact lens 1105. In this way, light 1106 intended for light therapy is only dispersed around a perimeter of a cornea 1107, minimizing its effect on normal vision.

In still other embodiments, an entire complimentary contact lens 1105 includes light scattering properties such as diffraction, refraction or reflection. Light scattering properties are designed such that they disperse only light 1106 of wavelengths emitted by embedded light sources 1104. This embodiment supports maximum dispersion of light 1106 wavelengths intended for light therapy within an eye 1108 while not causing dispersion of light wavelengths that would distort vision.

CONCLUSION

The present invention, as described above and as further defined by the claims below, provides methods and apparatus for delivering light therapy using eyeglasses with embedded light sources, using eyeglasses and complimentary contact lenses, or using contact lenses with embedded light sources.

What is claimed is:

1. A system for administering light therapy, the system comprising:
   a spectacle frame sized for wearing on a human being and configured to secure one or more optical lenses;
   a contact lens having an optic zone and a perimeter area, the contact lens includes light scattering areas in the perimeter area configured to diffuse light passing therethrough; and
   one or more light sources fixedly mounted to at least one of the spectacle frame or the one or more optical lenses, the one or more light sources configured to direct light onto the light scattering areas in the perimeter area of the contact lens.

2. The system for administering light therapy according to claim 1, wherein the one or more light sources comprises one or more light emitting diodes.

3. The system for administering light therapy according to claim 1, wherein the one or more light sources are configured to emit blue light at wavelengths of 470 to 480 nanometers at between 2000 and 3000 lux.

4. The system for administering light therapy according to claim 1, wherein the one or more light sources are configured to emit green light at wavelengths of 490 to 510 nanometers at between 300 to 400 lux.

5. The system for administering light therapy according to claim 1, further comprising one or more light sources mounted to the spectacle frame.

6. The system for administering light therapy according to claim 1, wherein the light scattering areas only disperse light of wavelengths emitted by the one or more light sources.

7. The system for administering light therapy according to claim 1, wherein the contact lens further comprises, an internal barrier for preventing light from the one or more light sources from being dispersed into the optical zone of the contact lens.

8. The system for administering light therapy according to claim 7, wherein light from the one or more light sources is dispersed by the contact lens into an area around the perimeter of a cornea.

* * * * *